United States Patent [19]

Tamano et al.

[11] Patent Number: 5,279,302
[45] Date of Patent: Jan. 18, 1994

[54] ULTRASONIC DOPPLER BLOOD FLOW MEASURING APPARATUS

[75] Inventors: Satoshi Tamano, Kashiwa; Hideki Nagata, Sagamihara; Koji Tanabe, Kashiwa, all of Japan

[73] Assignee: Hitachi Medical Corporation, Tokyo, Japan

[21] Appl. No.: 9,007

[22] Filed: Jan. 26, 1993

[30] Foreign Application Priority Data

Jan. 28, 1992 [JP] Japan .................................. 4-035858

[51] Int. Cl.$^5$ .................................................. A61B 8/00
[52] U.S. Cl. .................................................. 128/661.09
[58] Field of Search ............... 128/661.08, 661.09, 128/662.04, 660.05, 660.04, 661.10

[56] References Cited

U.S. PATENT DOCUMENTS 5,105,817  4/1992  Uchibori et al. ............... 128/661.08
5,156,152  10/1992 Yamazaki et al. ............. 128/661.09
5,190,044  3/1993  Kawasaki et al. ............. 128/661.08

Primary Examiner—William E. Kamm
Assistant Examiner—George Manuel
Attorney, Agent, or Firm—Antonelli, Terry, Stout & Kraus

[57] ABSTRACT

An ultrasonic Doppler blood flow measuring apparatus comprises a plurality of frame memories for storing information pieces about a blood flow speed in a unit of frame, circuits for comparing blood flow speed information pieces at corresponding addresses on the plurality of frame, memories and determining a speed difference, a circuit for comparing the speed difference with a predetermined threshold value and determining a blood flow at the corresponding address as an arterial flow when the speed difference exceeds the threshold value but as a venous flow when the speed difference is below the threshold value, and a circuit for displaying the determined arterial and venous flows in different colors.

12 Claims, 4 Drawing Sheets

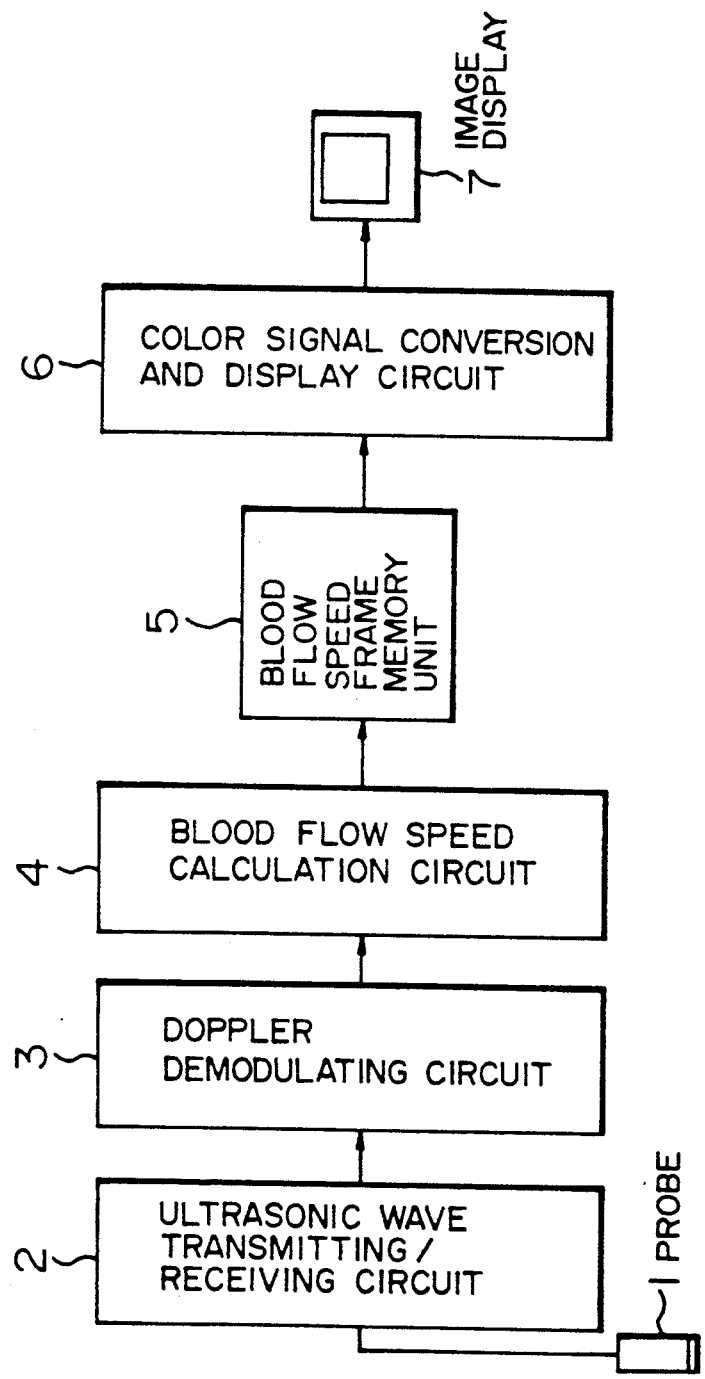

ULTRASONIC DOPPLER BLOOD FLOW MEASURING APPARATUS

BACKGROUND OF THE INVENTION

The present invention relates to an ultrasonic Doppler blood flow measuring apparatus in which an ultrasonic wave is transmitted to and received from a subject to provide a reflected echo signal and a signal caused to undergo a Doppler shift by a blood flow is derived from the reflected echo signal to display blood flow information two-dimensionally and more particularly to an ultrasonic blood flow measuring apparatus capable of determining which of arterial and venous flows a blood flow in a region of interest belongs to and displaying arterial and venous flows in coloring fashion.

A conventional ultrasonic Doppler blood flow measuring apparatus of this type comprises, as shown in FIG. 5, a probe 1 for transmitting and receiving an ultrasonic wave to and from a subject, an ultrasonic wave transmitting/receiving circuit 2 for controlling the probe 1 so as to cause it to transmit and receive the ultrasonic wave and amplifying a received reflected wave signal, a Doppler demodulating circuit 3 for deriving a frequency signal, caused to undergo a Doppler shift by a blood flow in the subject, from the reflected echo signal produced from the ultrasonic wave transmitting/receiving circuit 2, a blood flow speed calculation circuit 4 for calculating a blood flow speed in the subject by using the frequency signal from the Doppler demodulating circuit 3, a blood flow speed frame memory unit 5 for storing blood flow speed information from the blood flow speed calculation circuit 4, a color signal conversion and display circuit 6 for receiving data from the blood flow speed frame memory unit 5 and converting it into a color signal complying with a blood flow state, and an image display 7 for receiving the color signal from the color signal conversion and display circuit 6 to perform a coloring display. An ultrasonic wave is transmitted from the probe 1 to a vessel of the region of interest in the subject, and a Doppler shift frequency of an ultrasonic wave reflected from red blood corpuscles in the vessel and received is measured to obtain blood flow information which in turn is displayed two-dimensionally on the image display 7.

In the conventional ultrasonic Doppler blood flow measuring apparatus as above, data from the blood flow speed frame memory unit 5 is inputted to the color signal conversion and display circuit 6 and converted into a color signal complying with a blood flow speed to ensure that for example, a blood flow approaching the probe 1 can be coloring-displayed in a color of red system and a blood flow departing from the probe 1 ca be coloring-displayed in a color of blue system but any display as to which of arterial and venous flows the displayed blood flow belongs to cannot be obtained. In other words, the difference of directions of the blood flow can be determined and displayed in coloring fashion but it is impossible to determine which of arterial and venous flows the blood flow belongs to and to display a determined arterial or venous flow discriminatively in coloring fashion.

Under the circumstances, in the event that a blood flow is interrupted for some abnormal causes in a region of interest where a great number of vessels run complicatedly, for example, in the liver or kidney, a doctor or the like sometimes is not permitted to execute correct diagnosis if he does not know which of arterial and venous flows the blood flow in question belongs to. In such an event, the doctor or the like is forced to execute diagnosis while considering which of arterial and venous flows the blood flow portion where abnormality is occurring belongs to on the basis of knowledge of anatomy. Accordingly, it takes a long time to execute diagnosis and efficiency is degraded. In addition, the doctor or the like sometimes arises the individual difference in diagnostic judgment and correct diagnosis cannot be done.

SUMMARY OF THE INVENTION

Accordingly, the present invention intends to take care of the above problems and it is an object of the invention to provide an ultrasonic Doppler blood flow measuring apparatus which can determine which of arterial and venous flows a blood flow in a region of interest belongs to and display a determined arterial or venous flow discriminatively in coloring fashion To accomplish the above object, according to the present invention, in an ultrasonic Doppler blood flow measuring apparatus comprising a probe for transmitting and receiving an ultrasonic wave to and from a subject, an ultrasonic wave transmitting/receiving circuit for controlling the probe so as to cause it to transmit the ultrasonic wave and amplifying a received reflected wave signal, a Doppler demodulating circuit for deriving a frequency signal, caused to undergo a Doppler shift by a blood flow in the subject, from the reflected echo signal produced from the ultrasonic wave transmitting/receiving circuit, a blood flow speed calculation circuit for calculating a blood flow speed in the subject by using the frequency signal from the Doppler demodulating circuit, a blood flow speed frame memory unit for storing blood flow speed information pieces from the blood flow speed calculation circuit, a color signal conversion and display circuit for receiving data from the blood flow speed memory unit and converting it into a color signal complying with a blood flow state, and an image display for receiving the color signal from the color signal conversion and display circuit to perform a coloring display, a plurality of blood flow speed frame memories are provided in the memory unit, a maximum blood flow speed decision circuit for reading blood flow speed information pieces from corresponding addresses on the blood flow speed frame memories to decide which of the read-out blood flow speed information pieces is maximum and a minimum blood flow speed decision circuit for reading blood flow speed information pieces from the same corresponding addresses to decide which of the read-out blood flow speed information pieces is minimum are provided in parallel with each other, and a blood flow decision circuit for deciding, on the basis of the maximum and minimum blood flow speed information pieces from the speed decision circuits, which of arterial and venous flows the blood flow at the corresponding addresses belongs to and transmitting a decision signal to the color signal conversion and display circuit is provided.

In the present invention constructed as above, the color signal conversion and display circuit can convert data from the blood flow speed frame memories into a color signal complying with an arterial or venous flow and the image display can respond to the color signal to display an arterial or venous flow discriminatively in coloring fashion. Accordingly, the doctor or the like can determine the type of a blood flow in question instantaneously or at a glance without resort to diagnosis as in the past executed by considering which of arterial and venous flows the blood flow belongs to on the basis of an atomical knowledge while watching a display image This permits correct diagnosis to be done within a short period of time and efficiency of diagnosis can be improved.

BRIEF DESCRIPTION OF THE DRAWINGS

FIG. 5 is a block diagram showing a conventional ultrasonic Doppler blood flow measuring apparatus.

DESCRIPTION OF THE PREFERRED EMBODIMENTS

The invention will now be described in detail by way of example with reference to the accompanying drawings.

Figure 1:
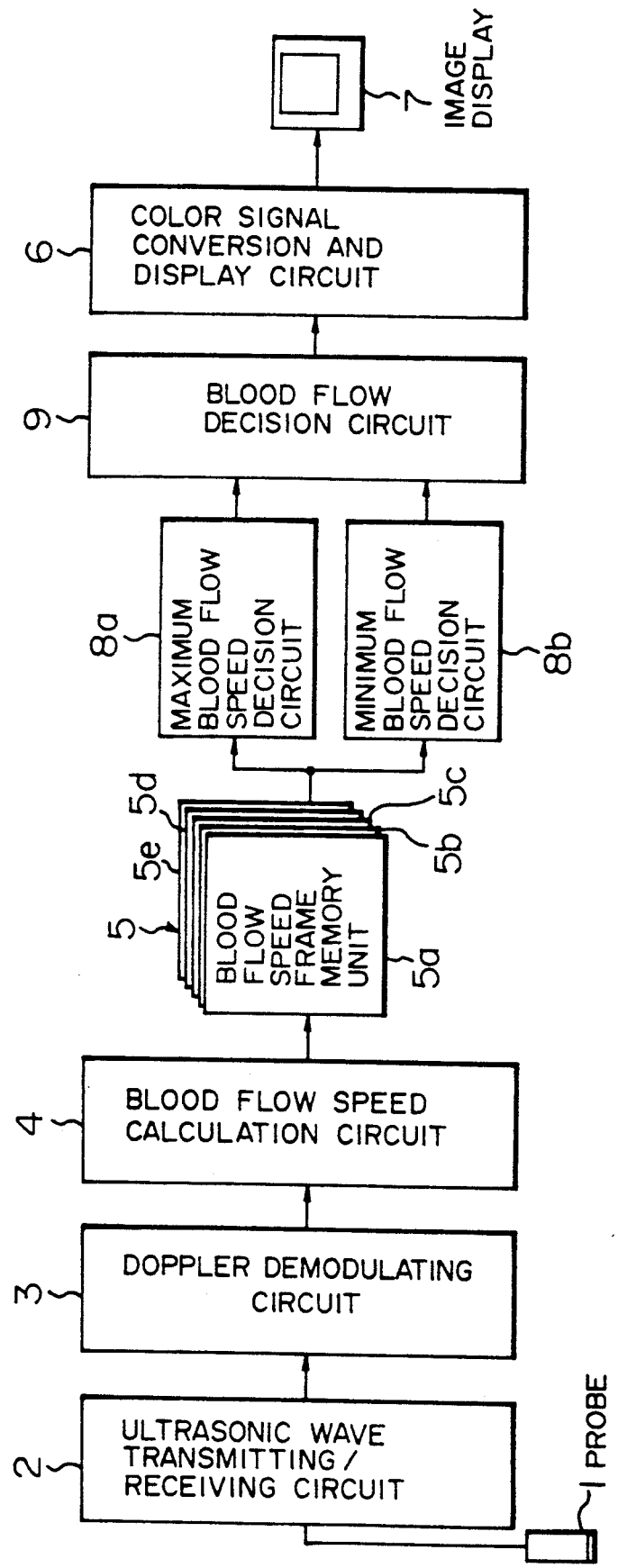
FIG. 1 is a block diagram showing an embodiment of an ultrasonic Doppler blood flow measuring apparatus according to the invention.

FIG. 1 shows, in block form, an embodiment of an ultrasonic Doppler blood flow measuring apparatus according to the invention. In the ultrasonic Doppler blood flow measuring apparatus, an ultrasonic wave is transmitted to and received from a subject to provide a reflected echo signal and a signal caused to undergo a Doppler shift is derived from the reflected echo signal to display blood flow information two-dimensionally. The apparatus comprises a probe 1, an ultrasonic wave transmitting/receiving circuit 2, a Doppler demodulating circuit 3, a blood flow speed calculation circuit 4, a blood flow speed frame memory unit 5, a color signal conversion and display circuit 6 and an image display 7 as well as a maximum blood flow speed decision circuit 8a, a minimum blood flow speed decision circuit 8b and a blood flow decision circuit 9.

The probe 1 is adapted to emit a ultrasonic wave to a region of interest in a subject and receive a reflected wave from the region and it incorporates, though not shown in the figure, a transducer serving as a generation source of ultrasonic wave and receiving a reflected wave. The ultrasonic wave transmitting/receiving circuit 2 is operative to control the prove 1 so as to cause it to generate the ultrasonic wave and amplify a received reflected wave signal and it incorporates, though not illustrated, a control circuit, a pulse generator and a receiving amplifier.

The Doppler demodulating circuit 3 is for receiving a reflected echo signal produced from the ultrasonic transmitting/receiving circuit 2 and deriving from the reflected echo signal a frequency signal caused to undergo a Doppler shift by a blood flow in the subject and it incorporates, though not illustrated, a local oscillator adapted to generate a reference frequency signal oscillating near a frequency of the ultrasonic wave subject to transmission/reception by the probe 1, a 90° phase shifter adapted to, for example, 90° shift the phase of the reference frequency signal generated from the local oscillator, a mixer circuit for multiplying the reflected echo signal by the reference frequency signal produced from the local oscillator or 90° phase shifter, and a high-cut filter for deriving a low-frequency component from the output of the mixer circuit.

The blood flow speed calculation circuit 4 is operative to calculate a blood flow speed in the subject by using the frequency signal subject to the Doppler shift (hereinafter referred to as a Doppler signal) delivered out of the Doppler demodulating circuit 3 and it incorporates an average speed calculation section for receiving Doppler signals and determining an average speed of a blood flow in a vessel in a region of interest and a speed variance calculation section for determining a speed variance of the blood flow. The blood flow speed frame memory unit 5 is adapted to temporarily store blood flow speed information delivered out of the blood flow speed calculation circuit 4.

In respect of data read out of the blood flow speed frame memory unit 5, the color signal conversion and display circuit 6 receives data obtained through the maximum blood flow speed decision circuit 8a, minimum blood flow speed decision circuit 8b and blood flow decision circuit 9, to be described later, and it converts the data into a color signal complying with a blood flow state represented by the data and converts that digital signal into a video signal. The image display 7 receives the color signal (video signal) to perform coloring display in, for example, red or blue and it is constructed of a television monitor for color display.

Specifically, in the present invention, the blood flow speed frame memory unit 5 consists of a plurality of, for example, five frame memories 5a, 5b, 5c, 5d and 5e, the blood flow speed frame memories 5a to 5e are followed by the maximum blood flow speed decision circuit 8a and minimum blood flow speed decision circuit 8b which are parallel with each other, and the decision circuits are followed by the blood flow decision circuit 9. The plural blood flow speed frame memories 5a to 5e sequentially store a plurality of time-sharing image data pieces and they are constructed such that when write of image data for one screen into one blood flow speed frame memory finishes, write of image data for the next screen into the next blood flow speed frame memory begins and thereafter the above write operations repeat sequentially.

Figure 2:
FIG. 2 is a graph showing characteristics of speed change of an arterial flow in living-body blood flow.
Figure 3:
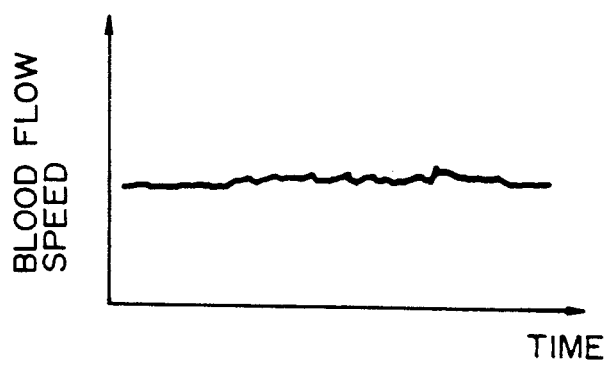
FIG. 3 is a graph showing characteristics of speed change of a venous flow in living-body blood flow.

The maximum blood flow speed decision circuit 8a reads blood flow speed information pieces from the same or corresponding addresses (X, Y) on the plurality of blood flow speed frame memories 5a to 5e at a time to decide which of the read-out blood flow speed information pieces is maximum and extract a maximum information piece. Similarly, the minimum blood flow speed decision circuit 8b reads blood flow speed information pieces from the same or corresponding addresses (X, Y) on the plural blood flow speed frame memories 5a to 5e at a time to decide which of the read-out blood flow speed information pieces is minimum and extract a minimum information piece. Decision of the maximum and minimum blood flow speeds is effected in order to determine discrimination between arterial and venous flows from behavior of a change in blood flow speed by taking advantage of the fact that in living-body blood flows, an arterial flow is strongly affected by the beat of the heart to exhibit such characteristics that the difference between maximum and minimum values of a blood flow speed within a certain interval of time is large as shown in FIG. 2 and on the other hand a venous flow is weakly affected by the beat of the heart to exhibit such characteristics that a blood flow speed is nearly constant to approximate a stationary flow as shown in FIG. 3.

The blood flow decision circuit 9 receives information pieces representative of the maximum and minimum blood flow speeds delivered out of the maximum blood flow speed decision circuit 8a and minimum blood flow speed decision circuit 8b, respectively, to determine the discrimination between arterial and venous flows and transmit a decision signal to the color signal conversion and display circuit 6. The decision circuit 9 decides the characteristics of blood flow shown in FIGS. 2 and 3 as follows. More particularly, an operator such as the doctor or the like studies behavior of a change in blood flow speed shown in FIGS. 2 and 3 to set a certain threshold value for the difference between the maximum and minimum blood flow speeds, and when a difference between blood flow speeds supplied from the maximum blood flow speed decision circuit 8a and minimum blood flow speed decision circuit 8b exceeds the threshold value set as above, he determines that a blood flow in a region of interest is an arterial flow but when the difference is below the threshold value, he determines that the blood flow is a venous flow. Such a decision as above is carried out throughout the overall field of each of the blood flow speed frame memories 5a to 5e. As for the threshold value, optimum threshold values for different regions of interest may be prepared on a table so that when the operator selects a region of interest, an optimum threshold value may be selected automatically.

A decision signal delivered out of the blood flow decision circuit 9 is applied to the color signal conversion and display circuit 6. On the basis of the inputted decision signal representative of an arterial or venous flow, the color signal conversion and display circuit 6 converts data determined as representative of an arterial flow into a color signal of, for example, red system and data determined as representative of a venous flow into a color signal of, for example, blue system. Thereafter, the respective color signals are converted into video signals. The video signals delivered out of the color signal conversion and display circuit 6 are inputted to the image display 7 to discriminatively display an arterial flow portion in coloring of, for example, red and a venous flow portion in coloring of, for example, blue. This permits the operator to instantaneously know a portion where an arterial flow prevails and a portion where a venous flow prevails by watching a display on the screen of the image display 7.

Figure 4:
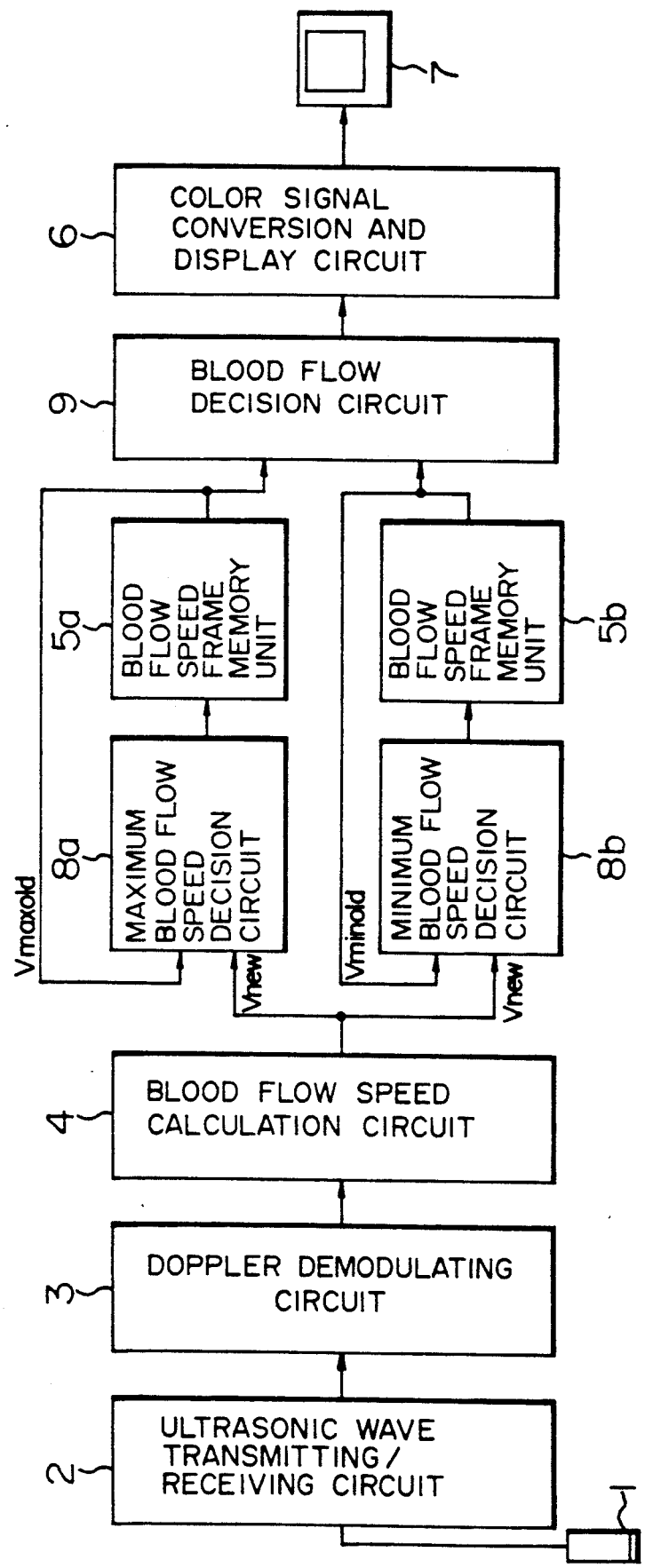
FIG. 4 is a block diagram showing a second embodiment of the invention.

FIG. 4 shows, in block form, a second embodiment of the invention. In the present embodiment, blood flow information from the blood flow speed calculation circuit 4 is inputted directly to a maximum blood flow speed decision circuit 8a and a minimum blood flow speed decision circuit 8b instead of to the plurality of, for example, five blood flow frame memories 5a to 5e shown in FIG. 1, the decision circuits 8a and 8b are followed by a single blood flow frame memory 5a and a single blood flow frame memory 5b, respectively, and data from the blood flow frame memories 5a and 5b is supplied to the blood flow decision circuit 9. In this case, the maximum blood flow speed decision circuit 8a is sequentially supplied with a new blood flow speed information piece $V_{new}$ calculated by the blood flow speed calculation circuit 4 and with a data piece $V_{maxold}$ representative of a blood flow speed which is maximum till then and which is read out of the first blood flow speed frame memory 5a storing the previous maximum blood flow speed data piece determined by the maximum blood flow speed decision circuit 8a. The minimum blood flow speed decision circuit 8b is sequentially supplied with the new blood flow speed information piece $V_{new}$ calculated by the blood flow speed calculation circuit 4 and with a data piece $V_{minold}$ representative of a blood flow speed which is minimum till then and which is read out of the second blood flow speed frame memory 5b storing the previous minimum blood flow speed data piece determined by the minimum blood flow speed decision circuit 8b. Each of the frame memories 5a and 5b is cleared in synchronism with the heartbeat or at constant time intervals.

With the above construction, the maximum blood flow speed decision circuit 8a compares a data piece $V_{new}$ with a data piece $V_{maxold}$ during a period of, for example, one beat and if $$V_{new} \geq V_{maxold}$$

stands, it determines the data piece $V_{new}$ as a new maximum blood flow speed data piece which in turn is stored in the succeeding first blood flow speed frame memory 5a and then transmitted to the blood flow decision circuit 9 succeeding the frame memory 5a. But if $$V_{new} < V_{maxold}$$

stands, the maximum blood flow speed decision circuit 8a determines the data piece $V_{maxold}$ per se as a maximum blood flow speed data piece and that maximum blood flow speed data piece, represented by the data piece $V_{maxold}$, is transmitted to the succeeding blood flow decision circuit 9 without updating the data in the first blood flow speed frame memory 5a.

Similarly, the minimum blood flow speed decision circuit 8b compares the data piece $V_{new}$ with a data piece $V_{minold}$ during the period of, for example, One beat and if $$V_{new} \leq V_{minold}$$

stands, it determines the data piece $V_{new}$ as a new minimum blood flow speed data piece which in turn is stored in the succeeding second blood flow speed frame memory 5b and then transmitted to the blood flow decision circuit 9 succeeding the frame memory 5b. But if $$V_{new} > V_{minold}$$

stands, the minimum blood flow speed decision circuit 8b determines the data piece $V_{minold}$ per se as a minimum blood flow speed data piece and that minimum blood flow speed data piece, represented by the data piece $V_{minold}$, is transmitted to the succeeding blood flow decision circuit 9 without updating the data in the second blood flow speed frame memory 5b.

The subsequent operation is similar t that in the first embodiment shown in FIG. 1, whereby a difference between two blood flow speeds read out of the frame memories 5a and 5b is compared with a threshold value and when the difference exceeds the threshold value, a blood flow at a read-out address is determined as an arterial flow but when the difference is below the threshold value, the blood flow is determined as a venous flow. Since in the second embodiment only the two blood flow speed frame memories suffice, the number of necessary frame memories can be reduced to reduce costs.

In the present invention, by providing in parallel the circuits for applying a signal from the blood flow speed frame memory unit directly to the color signal conversion and display circuit, arterial and venous flows can be discriminated from each other in coloring fashion and at the same time the approach and departure of a blood flow can also be discriminated from each other in coloring fashion.

We claim:

1. An ultrasonic Doppler blood flow measuring apparatus comprising:
   means for transmitting and receiving an ultrasonic wave to and from a subject;
   means for determining a blood flow speed in said subject from a received reflected echo signal;
   a plurality of frame memories for storing information pieces about said blood flow speed in a unit of frame;
   means for comparing information pieces about said blood flow speed at corresponding addresses on said plurality of frame memories to determine a speed difference;
   means for comparing said speed difference with a predetermined threshold value and for deciding which of arterial and venous flows a blood flow at each address belongs to; and
   means, responsive to outputs of said decision means, for displaying arterial and venous flows in different colors.

2. An ultrasonic Doppler blood flow measuring apparatus according to claim 1, wherein said means for determining a speed difference includes means for obtaining a maximum blood flow speed value and a minimum blood flow speed value from said blood flow speed information pieces.

3. An ultrasonic Doppler blood flow measuring apparatus according to claim 1, wherein said decision means determines a blood flow at the corresponding address as an arterial flow when said speed difference exceeds said threshold value but determines a blood flow at the corresponding address as a venous flow when said speed difference is below said threshold value.

4. An ultrasonic Doppler blood flow measuring apparatus according to claim 1, wherein said decision means comprises:
   a table on which threshold values for different regions of interest are described; and
   means for automatically reading a threshold value from said table when an operator selects a region of interest and comparing said read-out threshold value with said speed difference.

5. An ultrasonic Doppler blood flow measuring apparatus comprising:
   means for transmitting and receiving an ultrasonic wave to and from a subject;
   means for determining a blood flow speed in said subject from a received reflected echo signal;
   first and second frame memories for storing information pieces about said blood flow speed;
   means for comparing the magnitude of a speed represented by a blood flow speed information piece sequentially inputted to said first frame memory with that of a speed represented by a blood flow speed information piece which has already been stored in said first frame memory at an address corresponding to that of said inputted blood flow speed information piece, and for writing the larger comparison value into said first frame memory;
   means for comparing the magnitude of a speed represented by a blood flow speed information piece sequentially inputted to said second frame memory with that of a speed represented by a blood flow speed information piece which has already been stored in said second frame memory at an address corresponding to that of said inputted blood flow speed information piece, and for writing the smaller comparison value into said second frame memory;
   means for comparing said blood flow speed information pieces at corresponding addresses of said first and second frame memories to determine a speed difference information piece;
   means for comparing said speed difference information piece with a predetermined threshold value and deciding which of arterial and venous flows a blood flow at each address belongs to; and
   means responsive to outputs of said decision means to display arterial and venous flows in different colors.

6. An ultrasonic Doppler blood flow measuring apparatus according to claim 5, wherein said decision means determines a blood flow at the corresponding address as an arterial flow when said speed difference exceeds said threshold value but determines a blood flow at the corresponding address as a venous flow when said speed difference is below said threshold value.

7. An ultrasonic Doppler blood flow measuring apparatus according to claim 5, wherein said decision means comprises:
   a table on which threshold values for different regions of interest are described; and
   means for automatically reading a threshold value from said table when an operator selects a region of interest and comparing said read-out threshold value with said speed difference.

8. An ultrasonic Doppler blood flow measuring apparatus comprising:
   a probe for transmitting and receiving an ultrasonic wave to and from a subject;
   an ultrasonic wave transmitting/receiving circuit for controlling said probe so as to cause it to transmit the ultrasonic wave and amplifying a received reflected wave signal;
   a Doppler demodulating circuit for deriving a frequency signal caused to undergo a Doppler shift by a blood flow in said subject from the reflected echo signal produced from said ultrasonic wave transmitting/receiving circuit;
   a blood flow speed calculation circuit for calculating a blood flow speed in said subject by using said frequency signal from said Doppler demodulating circuit;
   a plurality of frame memories for storing blood flow speed information pieces from said blood flow speed calculation circuit;
   blood flow speed decision circuits for reading blood flow speed information pieces from corresponding addresses on said plurality of frame memories to compare magnitudes of a blood flow speed;
   a blood flow decision circuit for deciding on the basis of blood flow speed information pieces from said speed decision circuits which of arterial and venous flows said blood flow at the corresponding addresses belongs to;

a color signal conversion and display circuit responsive to a signal from said blood flow decision circuit to convert data from said frame memories into different color signals complying with arterial and venous flows; and an image display for receiving said color signals and displaying them in coloring fashion.

9. An ultrasonic Doppler blood flow measuring apparatus according to claim 8, wherein said blood flow speed decision circuit includes means for determining a maximum blood flow speed and a minimum blood flow speed.

10. An ultrasonic Doppler blood flow measuring apparatus according to claim 8, wherein said blood flow decision circuit includes means for comparing a blood flow speed difference with a predetermined threshold value assigned to individual regions of interest and determining a blood flow as an arterial flow when said difference exceeds said threshold value but as a venous flow when said speed difference is below said threshold value.

11. An ultrasonic Doppler blood flow measuring apparatus according to claim 10, wherein said blood flow decision circuit comprises:

a table on which threshold values for different regions of interest are described; and means for automatically reading a threshold value from said table when an operator selects a region of interest and comparing said read-out threshold value with said speed difference.

12. An ultrasonic Doppler blood flow measuring method comprising the steps of:

transmitting and receiving an ultrasonic wave to and from a subject;

determining a blood flow speed in said subject from a received reflected echo signal and storing information pieces about said blood flow speed in a plurality of frame memories in a unit of frame;

comparing blood flow speed information pieces at corresponding addresses on said plurality of frame memories and determining a speed difference;

comparing said speed difference with a predetermined threshold value, determining a blood flow at a portion where said speed difference exceeds said threshold value as an arterial flow and a blood flow at a portion where said speed difference is below said threshold value as a venous flow, and delivering decision signals; and displaying arterial and venous flows in different colors on the basis of said decision signals.

* * * * *